United States Patent
Kaylor et al.

(10) Patent No.: US 6,613,029 B1
(45) Date of Patent: Sep. 2, 2003

(54) VAPOR SWEPT DIAPER

(75) Inventors: Rosann Marie Kaylor, Cumming, GA (US); James Arthur Davis, Roswell, GA (US); Andrew Edsel Huntoon, Appleton, WI (US); Michael Tod Morman, Alpharetta, GA (US); Mary Garvie Weber, Tucson, AZ (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/301,492

(22) Filed: Apr. 28, 1999

(51) Int. Cl.$^7$ .............................................. A61F 13/15
(52) U.S. Cl. .................. 604/385.01; 604/367
(58) Field of Search ................. 604/358, 359, 604/367, 378, 385.01

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,881,491 A | 5/1975 | Whyte | 128/287 |
| 3,921,232 A | 11/1975 | Whyte | 5/91 |
| 4,340,563 A | 7/1982 | Appel et al. | 264/518 |
| 5,057,368 A | 10/1991 | Largman et al. | 428/397 |
| 5,069,970 A | 12/1991 | Largman et al. | 428/373 |
| 5,108,820 A | 4/1992 | Kaneko et al. | 428/198 |
| 5,108,827 A | 4/1992 | Gessner | 428/219 |
| 5,137,525 A | 8/1992 | Glassman | 604/385.1 |
| 5,277,976 A | 1/1994 | Hogle et al. | 428/397 |
| 5,330,459 A * | 7/1994 | Lavon et al. | 604/385.01 |
| 5,336,552 A | 8/1994 | Strack et al. | 428/224 |
| 5,364,382 A | 11/1994 | Latimer et al. | 604/378 |
| 5,382,400 A | 1/1995 | Pike et al. | 264/168 |
| 5,466,410 A | 11/1995 | Hills | 264/172.11 |
| 5,490,846 A | 2/1996 | Ellis et al. | 604/366 |
| 5,558,658 A | 9/1996 | Menard et al. | 604/385.1 |
| 5,810,797 A | 9/1998 | Menard et al. | 604/378 |
| 6,018,093 A * | 1/2000 | Roe et al. | 604/367 |

FOREIGN PATENT DOCUMENTS

| | | | |
|---|---|---|---|
| EP | 0 269 401 | 6/1988 | A41B/13/02 |
| WO | 95/00089 | 1/1995 | A61F/13/15 |
| WO | 98/47455 | 10/1998 | A61F/13/15 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

* cited by examiner

*Primary Examiner*—Dennis Ruhl
(74) *Attorney, Agent, or Firm*—Steven D. Flack

(57) ABSTRACT

There is provided a personal care product having a vapor sweep comprising a material which reacts with water or urine to form vapor at a rate capable of displacing at least 5, and preferably at least 10, percent of the air volume within said product per minute. This vapor generation sweeps water vapor and humidity from the personal care product, such as a diaper, and so it's believed will contribute to skin health. Materials that, upon reaction with water or urine, produce large volumes of carbon dioxide may be incorporated into the various components of standard personal care products to achieve the objective of this invention. Such materials include leavening agents. Additionally, a seal may be added to the personal care product to encourage the generated vapor to travel a longer path prior to exiting the product in order to maximize water vapor removal.

15 Claims, 2 Drawing Sheets

VAPOR SWEPT DIAPER

FIELD OF THE INVENTION

This invention relates to absorbent articles particularly absorbent structures that are useful in personal care products such as disposable diapers, incontinence guards, and childcare training pants and the like. More particularly, the invention relates to absorbent articles that have a portion designed for the release of volumes of vapor upon the insult of the article, thus driving moisture out of the article, reducing the humidity and, as a result, the detrimental effect on the skin of bodily exudates.

BACKGROUND OF THE INVENTION

Personal care products are absorbent articles including diapers, training pants, incontinence devices and the like. These products are designed to absorb and contain body exudates and are generally single-use or disposable items which are discarded after a relatively short period of use—usually a period of hours—and are not intended to be washed and reused. Such products are placed against or in proximity to the wearer's body to absorb and contain various exudates discharged from the body. All of these products typically include a liquid permeable bodyside liner or cover, a liquid impermeable outer cover or backsheet, and an absorbent structure disposed between the bodyside liner and outer cover. The liquid impermeable outer cover may be breathable, i.e., permeable to water vapor.

It has been found that urination can occur at rates as high as 15 to 20 milliliters per second and at velocities as high as 280 centimeters per second. The volume of urine released per occurrence can vary from about a nominal amount to about 100 ml. It's important for the absorbent article to rapidly uptake liquid to avoid excessive pooling of liquid on the body-facing surface of the bodyside liner in order to avoid leakage. Even if absorbed, however, any liquid in the article contributes to the overall humidity near the wearer skin, causing discomfort and potential skin health problems.

The problem of excessive humidity near the skin in an absorbent article has been addressed in the art through a number of means. U.S. Pat. No. 5,137,525 for example, uses mechanical means to increase airflow in the article. Breathable outer covers allow air and water vapor diffusion and have been mentioned previously.

Despite these attempts, the need exists for further improvement in the reduction of humidity within absorbent articles. In particular, there is a need for materials that can flush or sweep excess humidity from the article. Ideally, this sweeping or flushing should occur after or in response to insult and not on a continuous basis. The present invention provides for such improved moisture reduction within an absorbent article.

SUMMARY OF THE INVENTION

The objects of this invention are achieved by a personal care product having a vapor sweep comprising a material that reacts with water or urine to form vapor at a rate capable of displacing at least 5 percent, and preferably at least 10 percent, of the air volume within said product per minute. This vapor generation sweeps water vapor and humidity from the personal care product, such as a diaper, and so it's believed will contribute to skin health. Materials that, upon reaction with water or urine, produce large volumes of a nontoxic gas such as carbon dioxide may be incorporated into the various components of standard personal care products to achieve the objective of this invention. Such materials include leavening agents. Additionally, a seal may be added to the personal care product to encourage the generated vapor to travel a longer path prior to exiting the product in order to maximize water vapor removal.

DEFINITIONS

Figure 1:
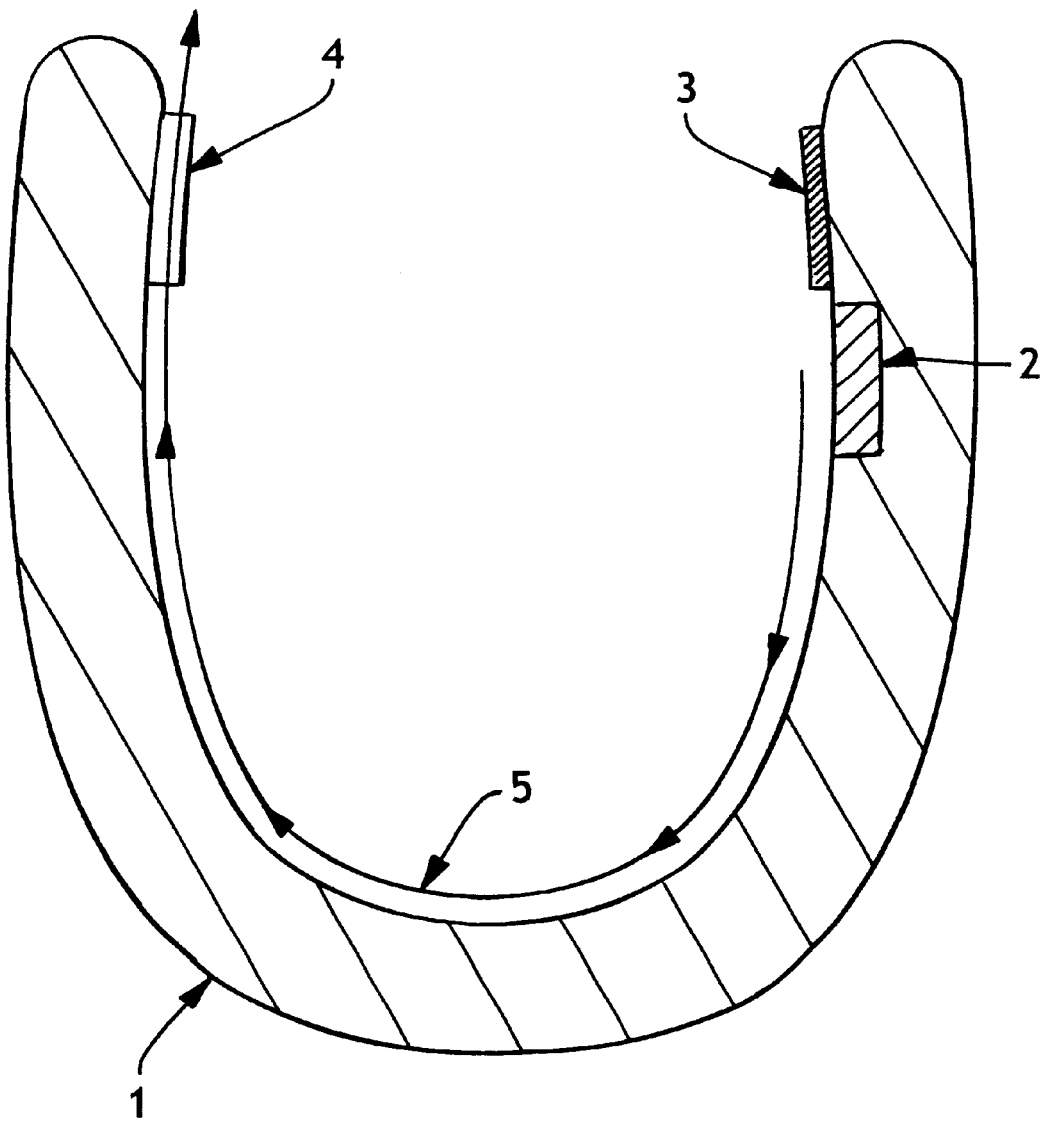
FIG. 1 is a drawing of a longitudinal cross section side view of a personal care product having a seal against the body and directing vapor flow in one direction.

"Disposable" includes being disposed of after usually a single use and not intended to be washed and reused.

"Front" and "back" are used throughout this description to designate relationships relative to the garment itself, rather than to suggest any position the garment assumes when it is positioned on a wearer.

"Hydrophilic" describes fibers or the surfaces of fibers, which are wetted by the aqueous liquids in contact with the fibers. The degree of wetting of the materials can, in turn, be described in terms of the contact angles and the surface tensions of the liquids and materials involved. A Cahn SFA-222 Surface Force Analyzer System, or a substantially equivalent system can provide equipment and techniques suitable for measuring the wettability of particular fiber materials. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous substance and/or material that flows and can assume the interior shape of a container into which it is poured or placed.

"Liquid communication" means that liquid such as urine is able to travel from one location to another location.

"Longitudinal" and "transverse" have their customary meanings. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis.

"Particles" refers to any geometric form such as, but not limited to, spherical grains, cylindrical fibers or strands, or the like.

"Spray" and variations thereof include forcefully ejecting liquid, either as a stream such as swirl filaments, or atomized particles through an orifice, nozzle, or the like, by means of an applied pressure of air or other gas, by force of gravity, or by centrifugal force. The spray can be continuous or non-continuous.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. Nos. 5,277,976 to Hogle et al., U.S. Pat. No. 5,466,410 to Hills and U.S. Pat. Nos. 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, and are generally smaller than 10 microns in average diameter.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

"Biconstituent fibers" refers to fibers, which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. John A. Manson and Leslie H. Sperling also discuss Bicomponent and biconstituent fibers in the textbook *Polymer Blends and Composites*, copyright 1976, by Plenum Press, a division of Plenum Publishing Corporation of New York, IBSN 0-306-30831-2, at pages 273 through 277.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales, which are placed in an opener/blender, or picker, which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

The volume of air between the skin and a liner in a personal car product, or the volume of air between the skin and the fabric of a garment, is considered by the inventors to be the "air volume" of the article.

"Personal care product" means diapers, training pants, absorbent underpants, adult incontinence products, wound care products like bandages, and other articles.

DETAILED DESCRIPTION

Traditional absorbent systems for personal care products may be generalized as having the functions of surge control and containment (retention) or SC.

Surge control materials, the "S" in SC, are provided to quickly accept the incoming insult and either absorb, hold, channel or otherwise manage the liquid so that it does not leak outside the article. The surge layer may also be referred to as an intake layer, transfer layer, transport layer and the like. A surge material must typically be capable of handling an incoming insult of between about 60 and 100 cc at an insult volumetric flow rate of from about 5 to 20 cc/sec, for infants, for example.

Containment or retention materials, the "C" in SC, must absorb the insult quickly and efficiently. They are in liquid communication with the surge layer and should be capable of pulling the liquid from the surge layer and absorbing the liquid without significant blocking of penetration of liquid further into the absorbent. Retention materials are often high rate superabsorbent materials such as blends of polyacrylate superabsorbent and fluff. These materials rapidly absorb and hold liquid.

In addition to the surge control and containment materials in traditional absorbent systems, recent work has introduced another layer interposed between the S and C layers and in liquid communication with them. This new layer is a distribution layer, producing a system with surge control, distribution and containment or "SDC".

Distribution materials, the "D" in SDC, must be capable of moving fluid from the point of initial deposition to where storage is desired. Distribution must take place at an acceptable rate such that the target insult area, generally the crotch area, is ready for the next insult. By "ready for the next insult" it is meant that sufficient liquid has been moved out of the target zone so that the next insult results in liquid absorption and runoff within acceptable volumes. The time between insults can range from just a few minutes to hours, generally depending on the age of the wearer.

Absorbent products such as, for example, diapers, generally also have a liner which goes against the wearer and a backsheet which is the most exterior layer. An absorbent product may also contain other layers as well.

The liner is sometimes referred to as a bodyside liner or topsheet and is adjacent the surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner. These include spunbond or meltblown webs of polyolefin, polyester, polyamide (or other like fiber forming polymer) filaments, or bonded carded webs of natural polymers (for example, rayon or cotton fibers) and/or synthetic polymers (for example, polypropylene or polyester) fibers. The nonwoven web can be surface treated with a selected amount of surfactant, such as about 0.28% Triton X-102 surfactant, or otherwise processed to impart the desired level of wettability and hydrophilicity. If a surfactant is used, it can be an internal additive that migrates to the surface or applied to the web by any conventional means, such as spraying, printing, dipping, brush coating and the like.

The surge layer is most typically interposed between and in intimate, liquid communicating contact with the bodyside liner and another layer such as a distribution or retention layer. The surge layer is generally subjacent the inner (unexposed) surface of bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer. Various woven and nonwoven webs and foams can be used to construct a surge layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded-carded web or an airlaid web composed of natural and/or synthetic fibers. The bonded-carded web may, for example, be a powder bonded carded web, an infrared bonded carded web, or a through-air bonded carded web. Further examples of surge materials may be found in U.S. Pat. No. 5,490,846 to Ellis et al. and in U.S. Pat. No. 5,364,382 to Latimer. Surge layers may be composed of a substantially hydrophobic material, and the hydrophobic material may optionally be treated with a surfactant or otherwise processed to impart a desired level of wettability and hydrophilicity. Surge layers can have a generally uniform thickness and cross-sectional area.

A distribution layer, if present, must be capable of moving fluid from the point of initial deposition to where storage is desired. Distribution must take place at an acceptable rate such that the target insult area, generally the crotch area, is ready for the next insult. The time between insults can range from just a few minutes to hours, generally depending on the age of the wearer. Materials from which the distribution layer may be made include woven fabrics and nonwoven webs. For example, the distribution layer may be a nonwoven fabric layer composed of a meltblown or spunbond web of polyolefin, polyester, polyamide (or other web-forming polymer) filaments. Such nonwoven fabric layers may include conjugate, biconstituent and homopolymer fibers of staple or other lengths and mixtures of such fibers with other types of fibers. The distribution layer also can be a bonded-carded web, an airlaid web or a wetlaid pulp structure composed of natural and/or synthetic fibers or a combination thereof.

Retention materials are typically cellulosic materials or superabsorbents or mixtures thereof. Such materials are usually designed to quickly absorb liquids and hold them, usually without release. Superabsorbents are commercially available from a number of manufactures including Dow Chemical Company of Midland, Mich. and Stockhausen Corporation of Greensboro, N.C. Retention materials may be zoned and their compositions chosen to move liquids away from the target zone to more remote storage locations. Such a design more efficiently uses the entire absorbent article. The retention component of a personal care product is also called the "absorbent core".

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Backings may also serve the function of a mating member for mechanical fasteners, in the case, for example, where a nonwoven fabric is the outer surface.

Despite the advantages of modern surge, distribution and retention materials, its been found that a small amount of liquid can still remain in contact with the skin for some time after urination into a personal care product. Even absent skin wetness, however, a higher humidity level persists in the product for some time after urination. This exposure to high humidity levels in a personal care product is also believed to be detrimental to the skin. A personal care product that actively sweeps or flushes water vapor away from the skin addresses this issue and, its believed, can help keep skin healthy.

The inventors have found that incorporating into a personal care product various materials that react with urine to generate vapor can achieve the objective of a positive sweep of water vapor from the article. These materials may be incorporated into any of the components of the article, though most likely would be incorporated into the liner, surge, distribution or retention layers.

One method of incorporating the vapor generating materials into a component may be by using fibers made from or containing such materials. If the liner, for example, were a nonwoven web made from fibers of vapor generating materials, vapor generation would begin immediately upon urination. Incorporating such fibers into more interior layers would result in some time delay as urine from an insult gradually advanced into the article. Alternatively, such fibers could be made from vapor permeable polymers and the vapor generating material could be contained within them. In this configuration, water vapor from urination would diffuse through the fiber to the interior where it would react with the vapor generating materials. Vapor produced in this way would then diffuse out of the fiber and sweep additional water vapor from the article.

Another method of incorporating vapor-generating materials into a personal care product is to place it into a bag made from, for example, meltblown or other nonwoven fibers. Such a bag could be placed between the liner and surge layers, between the surge and distribution or retention layers, or in other locations, and could be of any convenient shape. Water vapor could then diffuse into the bag and react with the vapor generating materials.

It's important that the vapor sweep move through the personal care product and so sweep the maximum amount of water vapor possible from the product. The generation of vapor, which then merely escaped immediately from the product, would have little effectiveness. One way to maximize the path of the generated vapor would be to seal part of the article against the wearer's skin in one area thus directing the vapor flow in the opposite direction. The seal need not be absolute; it merely must encourage most of the generated vapor to travel in another direction.

FIG. 1 shows a longitudinal cross sectional view of a personal care product having a seal disposed for contact against the body and directing vapor flow in one direction. In FIG. 1, the personal care product 1 has incorporated into it a vapor generating material 2 and a seal 3 that will go against the wearer's body in the front or back. The part opposite 4 the seal 3 allows vapor to pass from the product 1. The arrows 5 illustrate vapor flow within the product 1.

Figure 2:
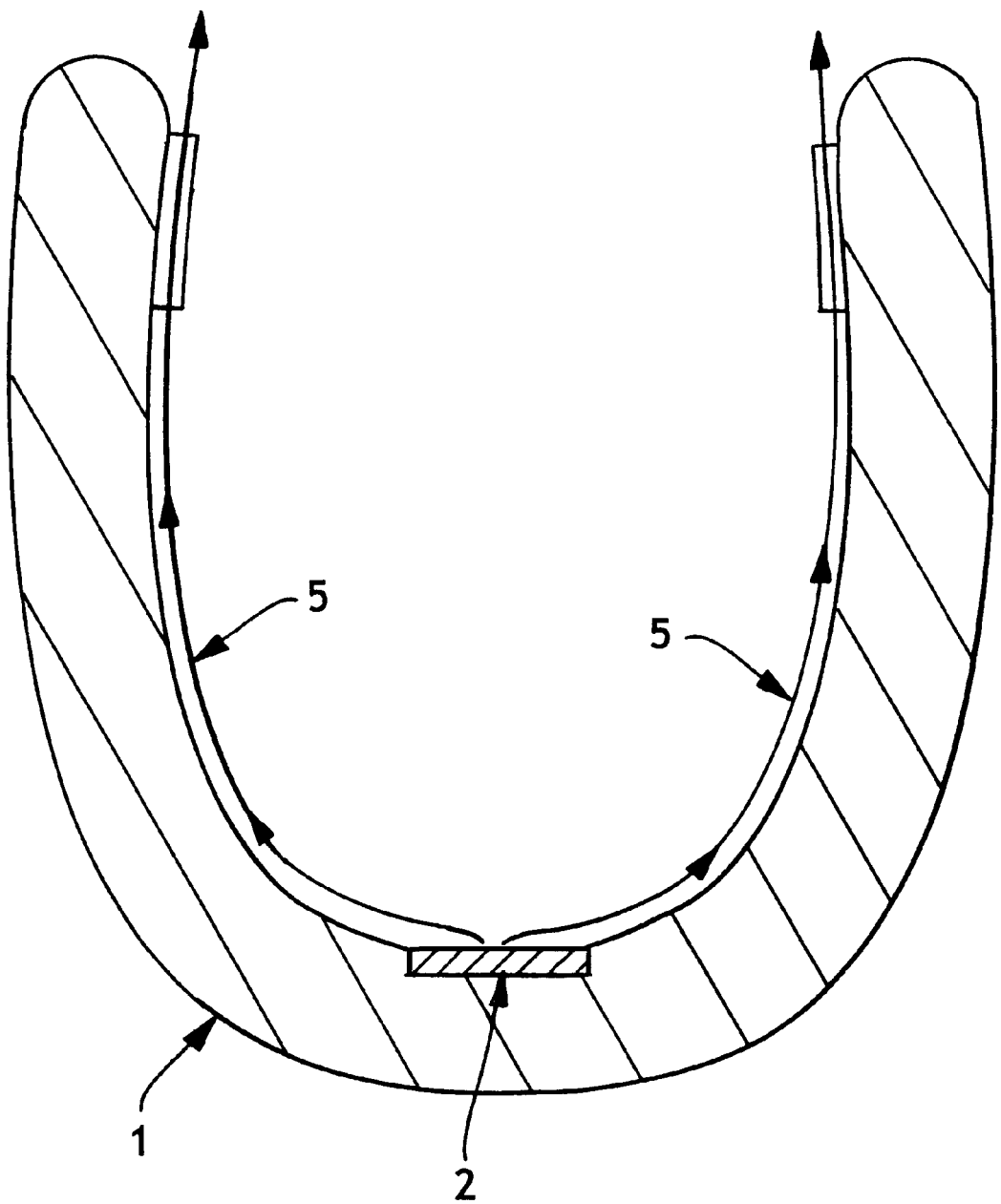
FIG. 2 is a drawing of a longitudinal cross section side view of a personal care product without a seal against the body and directing vapor flow in two directions.

FIG. 2 shows a longitudinal cross sectional view of a personal care product 1 without a seal against the body but with a vapor generating material 2 located such that vapor will travel up the front and back of the product and pass from the product 1. The arrows 5 illustrate vapor flow within the product 1.

It should be noted that FIGS. 1 and 2 are for illustrative purposes only and that the placement of the vapor generating materials is limited only by the imagination. The vapor generating materials may, of course, also be located in multiple locations within the product. In addition, seals may be placed in a product in the crotch or leg opening area, particularly with the configuration of FIG. 2, to encourage the vapor to travel the longest route.

In addition to the seal, another method of directing vapor flow within a personal care product is to create channels within the product. A channel in the center of an article in the longitudinal direction, for example, would direct more of the sweep vapor volume through the area most likely to receive a urine insult and would therefore probably be more effective. It is also possible to incorporate a breathable hydrophobic barrier layer or "spacer layer" (as described in U.S. patent application Ser. No. 08/994,530) into a personal care product. The spacer layer is placed between the absorbent layer and outer cover to reduce or eliminate the wet or clammy feeling that may develop on the outer portion of a personal care product due to condensation.

The vapor generating materials to be used in the practice of this invention must be capable of producing significant volumes of vapor upon reaction with water. If one assumes, for example, that the volume of air between the skin and a liner in a typical diaper is about 150 cm$^3$ and that it is desired to sweep 10 percent (by volume) of the air from the product per minute, about 15 cm$^3$ per minute would need to be generated. In a two hour period, about 1800 cm$^3$ would need to be generated.

Numerous vapors may be produced upon reaction with water, water vapor and/or urine that could produce the volumes necessary for the practice of this invention. It is obviously critical, however, that any such vapor generated within the product be safe, nonirritating and nontoxic for the wearer to be exposed to. One such suitable material to be generated within a personal care product at such low volumes is carbon dioxide, and it is the preferred vapor for practice of this invention. Since a mole of carbon dioxide ($CO_2$) weighs about 44 grams and occupies about 22.4 liters at standard temperature and pressure, about 3.5 grams of $CO_2$ would be needed to produce 1800 cm$^3$. The amount of material needed to generate this volume of $CO_2$ would depend on the chemical chosen and is within the ability of one skilled in the art to calculate.

Vapor generating chemicals suitable for the generation of $CO_2$ in sufficient quantities include leavening agents. Leavening agents are, for example, a combination of sodium bicarbonate with a weak acid such as creme of tartar, which is quite stable. Another example of a weak acid is citric acid. Other leavening agents react more slowly and include those made with sodium aluminum sulfate. Examples of commercially available leavening agents include Rexal baking powder and ARM & HAMMER® baking soda. Rexal baking powder contains sodium bicarbonate, sodium aluminum sulfate, cornstarch, calcium sulfate, calcium acid phosphate and monocalcium phosphate. More slowly reacting coated leavening agents are also suitable and may be desirable to produce a longer term sweeping effect. Combinations of vapor generating agents may also be used to produce, for example, a quick, high volume sweep upon insult, followed by a longer term, lower volume sweep.

It is also possible to use the vapor generating system of this invention to help reduce the humidity in work wear such as NOMEX® clothing or clothing worn for hazardous material handling as well as in surgical clothing. Any article of clothing, which has poor breathability resulting in perspiration and high humidity within the garment, would benefit from the application of this invention.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A personal care product for use adjacent the body of a wearer, and comprising a structure which defines a spatial path for the flow of vapor out from the product, the personal care product further comprising a vapor generating material that reacts with water or urine in order to generate vapor at a rate capable of displacing at least 5 percent of the air volume between a wearer of said product and said product, per minute, when said product is being worn, or at least at a rate of about 0.125 cc/sec, whereby as said vapor generating material reacts during product use, the vapor is directed so as to sweep vapor away from the product to a location out of the personal care product.

2. The personal care product of claim 1 wherein said vapor is generated at a rate of about 0.25 cc/sec.

3. The personal care product of claim 1 wherein said material is a leavening agent.

4. The personal care product of claim 3 wherein said leavening agent is selected from the group consisting of sodium bicarbonate, sodium aluminum sulfate and calcium sulfate.

5. The personal care product of claim 1 selected from the group consisting of diapers, training pants, absorbent underpants, adult incontinence products and wound care products.

6. The product of claim 5 wherein said personal care product is an adult incontinence product.

7. The product of claim 5 wherein said personal care product is a diaper.

8. The product of claim 5 further comprising a seal disposed to contact a wearer, whereby vapor is directed along a path during product use, between the body of the wearer and the product via said seal, to a location out of the product.

9. The product of claim 8 wherein said seal is disposed on a front of said product.

10. The product of claim 8 wherein said seal is disposed on a back of said product.

11. An article for use adjacent the skin of a wearer when worn, and of a structure defining a spatial path between the skin of the wearer and the article itself for the flow of vapor, the article including a vapor sweep system, with the vapor sweep system comprising a chemical that will react with water or urine to release vapor at a rate of at least 15 $cm^3$/min., whereby upon said chemical reaction, said vapor sweep system sweeps air contained between the skin of the wearer and the article itself to a location out of the article.

12. The article of claim 11 wherein said chemical is located within fibers.

13. The article of claim 11 wherein said chemical is located within at least one bag, into which water vapor can diffuse.

14. The article of claim 11, wherein said article is selected from the group consisting of personal care products and articles of clothing.

15. A personal care product for use adjacent the body of a wearer, and comprising a structure which defines a spatial path for the flow of vapor out from the product, the personal care product further comprising a vapor generating material that reacts with water or urine in order to generate vapor at a rate capable of displacing at least 5 percent of the air volume between a wearer of said product and said product, per minute, when said product is being worn, or at least at a rate of about 0.125 cc/sec, whereby as said vapor generating material reacts during product use, the vapor exits the personal care product.

* * * * *